United States Patent [19]

Moss

[11] Patent Number: 4,476,121

[45] Date of Patent: Oct. 9, 1984

[54] BOWEL EVACUANT AND METHOD OF TREATING CONSTIPATION

[76] Inventor: David W. Moss, 885 Park Ave., New York, N.Y. 10021

[21] Appl. No.: 470,979

[22] Filed: Mar. 1, 1983

[51] Int. Cl.³ .......................................... A61K 35/78
[52] U.S. Cl. .................................................. 424/195
[58] Field of Search ........................................ 424/195

[56] References Cited

U.S. PATENT DOCUMENTS 375,706  12/1887  Hoppel .............................. 424/195

OTHER PUBLICATIONS

Gilman et al., The Pharmacological Basis of Therapeutics, 5th Ed., 1976, pp. 976-983.

*Primary Examiner*—Albert T. Meyers
*Assistant Examiner*—John W. Rollins

[57] ABSTRACT

There is disclosed an orally administered composition useful in the treatment of constipation. The composition is a synergistic mixture of fruits, glycerine and compound senna which is efficacious at a dosage quantity far below that required of any of the ingredients when used alone.

5 Claims, No Drawings

BOWEL EVACUANT AND METHOD OF TREATING CONSTIPATION

BACKGROUND OF THE INVENTION

This invention relates to a composition which relieves constipation and aids in the evacuation of the contents of the lower bowel. More particularly, the invention relates to an improved composition which may be orally self administered, is pleasant tasting, storable under refrigeration for extended periods of time and fully excreatable by the body and therefore, free of drawbacks associated with many pharmaceutical preparations.

Constipation may be defined simply, as the infrequent and difficult passage of stool. It is manifest by a significant change in frequency of evacuation and an accompanying increased difficulty in passage. There are generally two major motor disturbances leading to constipation: spasticity which is predominately characterized as an irratable bowel syndrome; and atonicity, characterized by volumnous evacuation.

The most common form of constipation is known as an imaginery condition and is the result of a preconceived notion as to the definition of regularity. Such condition with an increased and abusive use of laxatives can lead to a secondary condition of excessive evacuation and consequent desensitization of urge and a reinforcement of the imaginary condition, whereupon the cycle repeats itself, going full circle each time.

Constipation is associated with difficulty in easily evacuating the bowel and doing so on a regular basis with a minimum of discomfort and strain. Constipation is believed to be caused by a variety of circumstances, including diet, physiological and physiological conditions, nervous tensions, side effects of medications, imbalances in the body's time clock, mechanical obstruction of the intestine and others.

Constipation may be grouped into the functional type associated with age, and chronic or acute types caused by one or more of the aforementioned circumstances.

In order to effectively provide for bowel evacuation it is preferable that the agent employed be efficacious in effecting the surface tension of and increase the water content of the stool, making it softer and therefore, easier to pass from the body. A softening of the feces combined with a mild degree of laxative effect thereby alleviates the symptoms of constipation without the discomfort of bowel distention, pain, cramping and other symptoms. A laxative effect suggests the elimination of a soft, formed stool, the major common characteristics are oral efficacy and activity that is primarily due to their physical properties within the intestinal lumen or to contact with the intestinal mucosa.

There are a variety of pharmaceutical preparations available, both by prescription as well as over the counter for the treatment of constipation. The more complex entities may act by a variety of mechanisms such as by increasing the tone and amplitude of gastric (especially antral) contractions, relaxation of the pylorci sphincter and duodenal bulb, increased peristalsis of the duodenum and jejunum resulting in accelerated gastric emptying and intestinal transit, increasing the resting tone of the lower esophageal sphincter, affecting motility of the colon and other actions.

Compositions which have the ability to carry out the above actions may be comprised of one or more of the following agents: metoclopramine salts, dehydrocholic acid, dioctyl sodium sulfosuccinate, potassium bitartrare, sodium bicarbonate, polyethylene glycol, bisacodyl, phenolphthalein, docusate sodium, mineral oil, hydrophilic colloids, Irish Moss, bran, glycerine suppositories, hypertonic phosphate or sulfates such as magnesium phosphate or epsom salt, castor oil, anthracine derivatives (senna, cascara and rhubarb) and homemade remedies of prunes or prune juice and the like.

A more traditional remedy has been enema, which not only is uncomfortable but creates a habit forming means of evacuation which can cause a life long dependence on artifical and invasive means of prompting the body to carry out a natural bodily function.

All of the foregoing aids, (with the exception of enema) whether taken as a liquid or in solid oral dosage form are unpleasant to the taste or impart a degree of discomfort in swallowing the solid dosage form or remembering to take it at a prescribed time which is often not convenient.

It is accordingly an object of the instant invention to avoid one or more drawbacks of the prior art.

It is another object of the invention to provide for a pleasant tasting, orally self administered preparation which is storage stable and may be eaten, such as in the form of a dessert or snack.

It is yet another object of the invention to provide for a bowel evacuant which may be taken over extended periods of time without regard to interference with other bodily functions.

It is a further object of the invention to provide for such an evacuant at a reasonable cost of manufacture and which may be so manufactured without the need of any special machinery.

Other and further objects of the invention will become more apparent from the following detailed description.

Detailed Description

In accordance with the aims of this invention there is provided a composition and method of treating constipation. The foregoing is accomplished in part, by the oral administration of a blend of ingredients, which individually may relieve constipation, but require quite large amounts to accomplish this end. It has now been found that by means of employing the compositions of the instant invention in the proportions as hereinafter set forth, there is a marked diminution in the quantity required for each active ingredient yet still retaining efficacy. This is totally unexpected in light of the amounts of such ingredients heretofore needed when used alone. In fact, it is quite surprising that the compositions of this invention are at all efficacious for their intended purpose as such low doses.

Broadly speaking, the invention includes a composition comprising a major portion of (a) at least one fruit selected from the group consisting of prunes, apricots and raisins; and (b) a minor portion including glycerine and compound senna. The active ingredients employed herein include one or more fruit constituents preferably as dried fruits, glycerine and compound senna powder. The preferred composition includes a blend of prune and a second fruit selected from apricots and raisin; glycerine and compound senna powder. It has been found that an efficacious mixture should be blended from components employed as about 24 parts fruit to about 1 part of a combination of glycerine/compound senna. Another good composition is about 48 parts fruit to about 1 part glycerine/compound senna. It is preferable that two fruits be employed comprising in combination 24 parts and a glycerine/compound senna mix of about ½ to 1 part. The relative proportions of the fruit to fruit combination may be varied widely within the minimum of about 24 parts total. The glycerine/compound senna mix may also be varied such that its total contribution does not fall below about ½ part, however, the relative amounts of these two ingredients to each other should not vary to widely and it is preferable that they be employed in about equal quantities to each other.

Once the ingredients have been selected, the fruits (preferably dried and pitted if fresh) should be combined with the glycerine and compound senna powder and thereafter suitably mixed so as to form a relatively homogeneous mixture. One or more suitable coloring agents or flavor extracts may be added in conventional amounts to vary the color or taste of the aforementioned composition. The composition thus made may be administered as is, or first be refrigerated to cause it to solidify and thereafter diced and taken in the form of a chewy mass, having a consistency somewhat like taffy.

It has surprisingly been found that this composition when administered in relatively minute amounts has any laxative properties at all, let alone being superior by a magnitude of about 10 fold over any such weight of the ingredients alone. It has been found that an equal degree of bowel evacuation cannot be effected by using an equal quantity of any one ingredient alone. Moreover, even a combination of all ingredients in equal parts will not produce the instantly attained effect.

It has now been found, however, that a highly efficacious laxative is provided by the administration of only about ½ teaspoon (2–3 cc) of this composition. Amounts varying from a low of about ¼ teaspoon to a high of about 2 teaspoons are especially efficacious. As aforesaid, none of the fruits alone or in combination are efficacious laxatives when taken in the amounts herein prescribed nor is compound senna efficacious in such small amounts. The compositions of this combination may be taken in varying amounts depending upon the intractability of the constipation. Generally, a single dose (5 cc) at bed time is adequate though lesser amounts will be efficacious with some individuals while others might need larger quantities (i.e. 1¼ to 3 teaspoons) and perhaps more than a single dose per day, i.e. morning and night.

The following examples are presented to define the invention more fully without any intention of being limited thereby. All parts and percentages are by weight unless indicated otherwise. In all instances dried fruit has been employed and the ingredients are homogenously blended, such as in a conventional mixing apparatus; there being nothing critical in the order of addition.

Where fresh fruits are employed it is preferable that after they are pitted they be allowed to dry so as to eliminate any excess water content which would interfere with the finished composition. The fresh de-pitted fruit may be dried whole or pureed first and then allowed to dry. In order to extend the shelf life of the mixture it should be refrigerated, though it may be employed as a gummy mass right after production. Refrigeration also increases patient compliance and ease of administration.

EXAMPLE I 8 oz. raisins
8 oz. prunes
8 oz. apricots
½ oz. glycerine
½ oz. compound senna powder

EXAMPLE II 12 oz. prunes
12 oz. apricots
½ oz. glycerine
½ oz. compound senna powder

EXAMPLE III 24 oz. prunes
½ oz. glycerine
½ oz compound senna powder

EXAMPLE IV 12 oz. prunes
12 oz. raisins
½ oz. glycerine
½ oz. compound senna powder

EXAMPLE V 12 oz. prunes
12 oz. apricots
¼ oz. glycerine
¼ oz. compound senna powder

EXAMPLE VI 8 oz. prunes
8 oz. apricots
8 oz. raisins
1 oz. glycerine
1 oz. compound senna powder While particular embodiments of the present invention have been described, it will be obvious to those skilled in the art that various changes and modifications can be made without departing from the spirit and scope of the invention and it is intended to cover, in the appended claims, all such modifications that are within the scope of this invention.

What is claimed is:

1. A composition useful in the treatment of constipation comprising (a) a first portion of at least two dried fruits selected from the group consisting of prunes, apricots and raisins in approximately equal amounts; and (b) a second portion including about equal quantities of glycerine and compond senna, the ratio of (a) to (b) being about 48:1 to about 12:1.

2. The composition as defined in claim 1 further including an effective amount of a flavor and/or coloring agent.

3. A method of treating constipation comprising orally administering an effective amount of a composition as defined in claim 1.

4. A method as defined in claim 3 wherein said amount is about one-quarter to about two teaspoons of said composition.

5. A method as defined in claim 3 wherein said composition is taken daily.

* * * * *